(12) United States Patent
Pillai et al.

(10) Patent No.: US 6,261,566 B1
(45) Date of Patent: Jul. 17, 2001

(54) COSMETIC COMPOSITIONS CONTAINING MULBERRY EXTRACT AND RETINOIDS

(75) Inventors: Sreekumar Pillai, Wayne; Manisha Narayan Mahajan, Westwood; David Joseph Pocalyko, Wayne; Stewart Paton Granger, Paramus; Bijan Harichian, Warren, all of NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/664,166

(22) Filed: Sep. 18, 2000

Related U.S. Application Data

(60) Provisional application No. 60/160,969, filed on Oct. 22, 1999.

(51) Int. Cl.$^7$ .............................. A01N 65/00; A61K 35/78
(52) U.S. Cl. ..................... 424/195.1; 424/60; 424/401
(58) Field of Search .................... 424/195.1, 401, 424/60

(56) References Cited

U.S. PATENT DOCUMENTS

| | | | |
|---|---|---|---|
| 5,332,575 | 7/1994 | Redziniak et al. | 424/450 |
| 5,607,692 | 3/1997 | Ribier et al. | 424/450 |
| 5,676,948 | 10/1997 | Bonte et al. | 424/195.1 |
| 5,676,949 | 10/1997 | Bonte et al. | 424/195.1 |
| 5,980,904 | * 11/1999 | Leverett et al. | 424/195.1 |
| 6,120,758 | 9/2000 | Siddiqui et al. | 424/78.02 |

FOREIGN PATENT DOCUMENTS

| | | |
|---|---|---|
| 0 815 838 | 1/1998 | (EP) . |
| 0 887 070 | 12/1998 | (EP) . |
| 2 661 829 | 11/1991 | (FR) . |
| 2 666 226 | 3/1992 | (FR) . |
| 98/06412 | 2/1998 | (WO) . |
| 99/55352 | 11/1999 | (WO) . |
| 00/02535 | 1/2000 | (WO) . |

OTHER PUBLICATIONS

Roos et al., Retinoid Metabolism in the Skin, Pharmacological Reviews, vol. 50, No. 2, pp. 315–333.

Elder et al., Retinoid Induction of CRABP 11mRNA in Human Dermal Fibroblasts; Use as a Retinoid Bioassay, The Society for Investigative Dermatology, Inc., vol. 106, No. 3, Mar. 1996, pp. 517–521.

* cited by examiner

*Primary Examiner*—Herbert J. Lilling
(74) *Attorney, Agent, or Firm*—Radha Masilamani

(57) ABSTRACT

Cosmetic skin care compositions containing mulberry extract in combination with selected retinoids.

3 Claims, No Drawings

COSMETIC COMPOSITIONS CONTAINING MULBERRY EXTRACT AND RETINOIDS

This application claims the benefit of U.S. provisional application No. 60/160,969 filed Oct. 22, 1999.

FIELD OF THE INVENTION

Cosmetic compositions containing mulberry extract in combination with retinoids and methods of conditioning skin by applying such compositions to the skin.

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and as skin repair and renewal agents. Retinoic acid has been used to treat a variety of skin conditions such as acne, wrinkles, psoriasis, age spots and skin discoloration.

Within the cells, retinol and retinoic acid are bound to specific cellular binding proteins, 2 of the major proteins are CRABP-1 and 2 (Roos et al., Pharmacological reviews: 50, 315–333, 1998). These proteins act in regulating the intracellular concentration of retinoids by acting as both storage or shuttle proteins in retinoid metabolism. The levels of this protein are regulated by the amount of retinoic acid within the cells. Higher cellular levels of retinoids increase the expression of CRABP-2. Therefore, the amount of this protein in the cells, is a measure of the retinoid activity of the cells. Skin cells contain CRABP-2 both in the epidermis and the dermis. CRABP-2 response to retinoid administration in fibroblasts in vitro is used as a reproducible measure of retinoid bioactivity that predict human skin responses (Elder et al., J. Invest. Dermatol., 106: 517–521, 1996). Therefore, CRABP-2 expression of fibroblasts is a measure of retinoid activity leading to various cosmetic skin benefits (antiaging, anti wrinkling, skin conditioning etc.).

Cosmetic compositions containing mulberry and retinoids have been disclosed. See for instance EP 815838 (Shiseido), EP887070 (Kibun Food Chemifa Co.), U.S. Pat. Nos. 5,676, 948, 5,676,949, and 5,607,692. U.S. Pat. No. 5,332,575 discloses a method of targeting melanocytes with a compound containing a fucose residue to bind the product to the melanocyte membrane. A cosmetic composition is exemplified containing dry mulberry root bark extract at 0.5% level. In another example, beta carotene or 0.25% vitamin A propionate is employed.

The present invention is based in part on the discovery that mulberry extract in combination with selected retinoids exhibit synergy, when combined within a specific ratio range.

SUMMARY OF THE INVENTION

The present invention includes a cosmetic skin care composition comprising:
(i) a glycolic extract of mulberry root in an amount of from 0.00001 to 10 wt. %,
(ii) a retinoid selected from the group consisting of retinyl acetate, retinyl palmitate and retinyl linoleate, and
(iii) a cosmetically acceptable vehicle, wherein the weight ratio of retinyl acetate to the mulberry extract is in the range of from 1:80 to 120:1,
the weight ratio of retinyl linoleate to the mulberry extract is in the range of from 1:8 to 120:1, and
the weight ratio of retinyl palmitate to the mulberry extract is in the range of from 1:16 to 6:1.

The present invention also includes a method of improving or preventing the condition of wrinkled, lined, dry, flaky, aged or photodamaged skin and improving skin thickness, elasticity, flexibility, radiance, glow and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to reduce the deteriorative changes.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

The mulberry extract suitable for use in the present invention is a glycolic extract from the root of white mulberry. White mulberry is also known as *Morus alba*. The extract may be obtained from Bioland (South Korea).

In general, the amount of the mulberry extract in the inventive compositions is in the range of from 0.001% to 20% by weight composition. Preferably in order to lower cost and maximize the effect the amount of the mulberry extract is in the range of from 0.01 to 10% and most preferably is in the range of from 0.1% to 5%.

The inventive compositions further comprise a retinoid selected from the group consisting of retinyl acetate, retinyl plamitate and retinyl linoleate. It has been found that these retinoids, act synergistically with the mulberry extract, when the reinoid and the mulberry extract are combined in a specific weight ratio: the weight ratio of retinyl acetate to the mulberry extract is in the range of from 1:80 to 120:1, preferably from 1:8 to 12:1, most preferably from 1:8 to 1.2:1; the weight ratio of retinyl linoleate to the mulberry extract is in the range of from 1:8 to 120:1, preferably from 1:8 to 12:1, most preferably from 1:8 to 1.2:1 of and the weight ratio of retinyl palmitate to the mulberry extract is in the range of from 1:16 to 6:1, preferably from 1:8 to 8:1, most preferably from 1:8to 1.2:1.

The composition according to the invention also comprises a cosmetically acceptable vehicle to act as a diluant, dispersant or carrier for the mulberry extract and the retinoid in the composition, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical cosmetic application to human skin, especially as an agent for conditioning, moisturizing and smoothening the skin, and preventing or reducing the appearance of lined, wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The following specific examples further illustrate the invention, but the invention is not limited thereto. In all examples, resveratrol was obtained from Sigma. Retinoids were obtained from Sigma. Student t-test was used to calculate all p-values.

EXAMPLES

The following methods were employed:

(1) Cell culture method:

Human adult fibroblasts obtained from sun-protected inner arm of 25–30 year female volunteer were used in this. Cells were grown in 1:1 DMEM/Hams F12 media containing 10% FBS, maintained at 37° C. in a 5% CO2 atmosphere under normal atmospheric oxygen tension. Third passage adult fibroblasts were grown in DMEM media with 10% FBS in 12-well plates at a seeding density of 40,000 cells/ml/well. The cells at 80% confluence were rinsed in serum free and phenol red free (PRF) DMEM media twice. Pre-treatment with phyto-active for 4 hours was conducted and then dosed with retinoids and was incubated for 48 hours. After the incubation, the wells were washed twice with 1×PBS and the cell monolayer was harvested in 100 $\mu$l cell lysis buffer (contains 1×PBS, 1% TritonX, 0.5% sodium deoxycholate, 0.1% SDS containing protease inhibitor (10 mg/ml PMSF in isopropanol, 10 μl/ml). The suspension was spun at 14000 rpm for 10 minutes, the supernatant collected and an aliquot of this supernatant was used for protein quantification. Protein concentration was determined using Pierce protein kit. The remainder of 100 μl supernatant (cell lysate) was denatured in a mixture of 40 μl sample buffer (NOVEX) and 0.5% Beta mercaptoethanol (BME) and by boiling the sample for 5 minutes. Equal amount of protein was then loaded onto 16% Tris-glycine gels for protein analysis by SDS page and Western Immuno-blotting for Crabp-2 protein expression.

3. Detection of Cellular Retinoic Acid Binding Protein 2 (CRABP-2) in fibroblasts and pig skin biopsies:

To measure the levels of CRABP-2 in the fibroblast and pig skin extracts prepared as described above, the cell supernatant was re-suspended in 4×sample buffer and 10% BME, boiled for 5 minutes and used for western blotting. Equal amounts of protein were loaded onto 16% Tris-glycine gels for CRABP-2 protein analysis by SDS page and Western Immuno-blotting. The gels were transferred to nitrocellulose blots and Western Blotting was carried out using monoclonal antibodies to CRABP-2 according to standard procedures. The CRABP-2 protein band was visualized in the Western Blots using the chemiluminescence system obtained from Santa Cruz Biotechnology (SantaCruz, Calif.). The bands in the film were quantitated by densitometric scanning, the data from triplicate samples were calculated as % of control and expressed in the following tables as % increase over control (with control as 100%) +/−SD of triplicates.

1. Calculations of retinoid:mulberry ratio

Mulberry extract used in these studies contain 2% solids. Therefore, 1 μl of mulberry extract added to 1 ml medium in these studies correspond to 0.1% extract×0.02% solids= 0.002% mulberry solids.

1 μM retinoid corresponds to approximately 500 ug/l of retinyl ester; which is equvalant to 50 ug/100 ml or 0.00005% of retinyl esters.

Therefore 1 μM retinod: 1 μl mulberry extract used in this in vitro assay system has a ratio of 0.00005 to 0.002 or a ratio of 1:80.

The different ratios of retinoids to mulberry used in the in vitro studies described in this patent and potential concentrations of retinoids to mulberry to fit this ratio in formulations which can be used in skin care products are shown in the Table 1 below.

TABLE 1

| Ratios (Ret:Mulberry) | In Vitro concentrations used to fit the ratios (μM retinoid: μl mulberry/ml) | Concentrations in formulations for use in skin care products to fit the ratio |
|---|---|---|
| 1:80 | 1 μM: 1 μl/ml | 0.001% retinoid: 4% extract |
|  | 100 μM: 0.1 μl/ml |  |
| 1:16 | 500 μM: 0.1 μl/ml | 0.005% retinoid: 4% extract |
|  |  | 0.001% retinoid: 0.8% extract |
| 1:8 | 1 μM: 0.1 μl | 0.01% retinoid: 4% mulberry extract |
|  | 100 nM: 0.01 μl | 0.005%: 2% |
| 1:1.6 | 500 nM: 0.01 μl | 0.05% retinoid: 4% extract |
|  |  | 0.01% retinoid: 0.8% extract |
| 1:0.8 or 1.2:1 | 10 μM: 0.1 μl | 0.05% retinoid: 2% extract |
|  | 1 μM: 0.01 μl | 0.12% retinoid: 5% extract |
|  | 100 nM: 0.001 μl | 0.1% retinoid: 8% extract |
| 12:1 | 1 μM: 0.001 μl | 0.12% retinoid: 0.5% extract |
|  |  | 1.2% retinoid: 5% extract |
| 120:1 | 10 μM: 0.001 μl | 1.2% retinoid: 0.5% extract |
|  |  | 0.6% retinoid: 0.25% extract |

It can be seen from Table 1 that the ratios cover the useful range of retinoids from 0.007% to 1.2% and the mulberry extract from 0.5% to 8%.

Tables 2–10 below show the CRABP-2 expression of fibroblasts in experiments using retinyl linoleate, retinyl palmitate and retinyl acetate with mulberry extract in different ratios from 1:80 (Tables 2,3), 1:16 (Table 4), 1:8 (Table 5), 1:16 (Table 6), 1:2:1 (Table 7), 6:1 (Table 8), 12:1 (Table 9) or 120:1 (Table 10). Table 11 summarizes all the data from Tables 2–10.

TABLE 2

1 μM retinyl esters and 1 μl mulberry extract (retinoid: mulberry ratio = 1:80)

| Groups | CRABP-2 levels | As % of control | p value vs. control | p value vs. retinoid | p value vs. mulberry | Synergy |
|---|---|---|---|---|---|---|
| Control | 0.92+/−0.16 | 100+/−17 | 1 |  |  |  |
| Retinyl Palmitate | 1.41+/−0.1 | 152+/−11 | 0.0116 | 1 |  |  |
| Retinyl linoleate | 1.04+/−0.36 | 112+/−38 | 0.635 | 1 |  |  |

TABLE 2-continued

1 μM retinyl esters and 1 μl mulberry extract (retinoid: mulberry ratio = 1:80)

| Groups | CRABP-2 levels | As % of control | p value vs. control | p value vs. retinoid | p value vs. mulberry | Synergy |
|---|---|---|---|---|---|---|
| Retinyl acetate | 2.58+/−0.09 | 278+/−10 | 0.0001 | 1 | | |
| Mulberry | 0.99+/−0.04 | 106+/−4 | 0.64 | | 1 | |
| Mulb + ret. palmitate | 1.22+/−0.55 | 131+/−59 | 0.426 | 0.576 | 0.614 | No |
| Mulb + ret. Linoleate | 0.4+/−0.1 | 43+/−11 | 0.009 | 0.041 | 0.0051 | No |
| Mulb + ret. acetate | 4.26+/−0.75 | 460+/−80 | 0.0016 | 0.018 | 0.0099 | Yes |

TABLE 3

100 nM retinyl esters and 0.1 μl mulberry extract (retinoid: mulberry ratio = 1:80)

| Groups | CRABP-2 levels | As % of control | p value vs. control | p value vs. retinoid | p value vs. mulberry | Synergy |
|---|---|---|---|---|---|---|
| Control | 1.33+/−0.21 | 100+/−15 | 1 | | | |
| Retinyl Palmitate | 2.35+/−0.51 | 177+/−38 | 0.032 | 1 | | |
| Retinyl linoleate | 2.12+/−0.19 | 159+/−14 | 0.0085 | 1 | | |
| Retinyl acetate | 1.47+/−0.27 | 111+/−20 | 0.5 | 1 | | |
| Mulberry | 1.2+/−0.1 | 90+/−7.0 | 0.392 | | 1 | |
| Mulb + ret. palmitate | 1.66+/−0.39 | 124+/−29 | 0.269 | 0.135 | 0.122 | No |
| Mulb + ret. Linoleate | 2.96+/−0.86 | 222+/−65 | 0.033 | 0.177 | 0.024 | No |
| Mulb + ret. acetate | 2.25+/−0.76 | 169+/−57 | 0.114 | 0.172 | 0.077 | No |

TABLE 4

500 nM retinyl esters and 0.1 μl mulberry extract (retinoid: mulberry ratio = 1:16)

| Groups | CRABP-2 levels | As % of control | p value vs. control | p value vs. retinoid | p value vs. mulberry | Synergy |
|---|---|---|---|---|---|---|
| Control | 1.33+/−0.21 | 100+/−15 | 1 | | | |
| Retinyl Palmitate | 1.43+/−−0.2 | 107+/−15 | 0.57 | 1 | | |
| Retinyl linoleate | 2.13+/−0.02 | 160+/−2.0 | 0.01 | 1 | | |
| Retinyl acetate | 2.05+/−0.06 | 153+/−5.0 | 0.02 | 1 | | |
| Mulberry | 1.2+/−0.1 | 90+/−7.0 | 0.392 | | 1 | |
| Mulb + ret. palmitate | 3.64+/−0.43 | 273+/−32 | 0.0011 | 0.0013 | 0.00065 | Yes |
| Mulb + ret. Linoleate | 2.41+/−0.33 | 181+/−24 | 0.0085 | 0.328 | 0.0036 | No |
| Mulb + ret. acetate | 5.03+/−0.80 | 378+/−60 | 0.0015 | 0.015 | 0.0013 | Yes |

TABLE 5

1 μM retinyl esters and 0.1 μl mulberry extract (retinoid: mulberry ratio = 1:8)

| Groups | CRABP-2 levels | As % of control | p value vs. control | p value vs. retinoid | p value vs. mulberry | Synergy |
|---|---|---|---|---|---|---|
| Control | 0.79+/−0.17 | 100+/−22 | 1 | | | |
| Retinyl Palmitate | 2.13+/−0.99 | 270+/−125 | 0.081 | 1 | | |
| Retinyl linoleate | 0.966+/−0.65 | 126+/−82 | 0.624 | 1 | | |
| Retinyl acetate | 2.23+/−0.5 | 283+/−63 | 0.0094 | 1 | | |
| Mulberry | 1.37+/−0.16 | 173+/−20 | 0.013 | | 1 | |
| Mulb + ret. palmitate | 5.27+/−0.61 | 667+/−77 | 0.000263 | 0.0095 | 0.00441 | yes |

TABLE 5-continued

1 μM retinyl esters and 0.1 μl mulberry extract (retinoid: mulberry ratio = 1:8)

| Groups | CRABP-2 levels | As % of control | p value vs. control | p value vs. retinoid | p value vs. mulberry | Synergy |
|---|---|---|---|---|---|---|
| Mulb + ret. Linoleate | 3.34+/−0.57 | 422+/−73 | 0.0045 | 0.026 | 0.0092 | yes |
| Mulb + ret. cetate | 3.97+/−0.18 | 502+/−23 | 0.00029 | 0.021 | 0.00045 | yes |

TABLE 6

500 nM retinyl esters and 0.01 μl mulberry extract (retinoid: mulberry ratio = 1: 1.6)

| Groups | CRABP-2 levels | As % of control | p value vs. control | p value vs. retinoid | p value vs. mulberry | Synergy |
|---|---|---|---|---|---|---|
| Control | 1.33+/−0.21 | 100+/−15 | 1 | | | |
| Retinyl Palmitate | 1.43+/−0.2 | 107+/−15 | 0.57 | 1 | | |
| Retinyl linoleate | 2.13+/−0.02 | 160+/−2 | 0.01 | 1 | | |
| Retinyl acetate | 2.05+/−0.06 | 153+/−5.0 | 0.02 | 1 | | |
| Mulberry | 1.4+/−0.2 | 105+/−15 | 0.67 | | 1 | |
| Mulb + ret. palmitate | 3.66+/−0.42 | 275+/−31 | 0.001 | 0.001 | 0.001 | Yes |
| Mulb + ret. Linoleate | 4.19+/−0.06 | 315+/−5.0 | 0.00005 | 0.00004 | 0.000002 | Yes |
| Mulb + ret. acetate | 3.37+/−0.23 | 253+/−17 | 0.002 | 0.016 | 0.022 | Yes |

TABLE 7

100 nM retinyl esters and 0.001 μl mulberry extract (retinoid: mulberry ratio = 1:0.8 OR 1.2:1)

| Groups | CRABP-2 levels | As % of control | p value vs. control | p value vs. retinoid | p value vs. mulberry | Synergy |
|---|---|---|---|---|---|---|
| Control | 1.33+/−0.21 | 100+/−15 | 1 | | | |
| Retinyl Palmitate | 2.35+/−0.51 | 177+/−38 | 0.032 | 1 | | |
| Retinyl linoleate | 2.12+/−0.19 | 159+/−14 | 0.0085 | 1 | | |
| Retinyl acetate | 1.47+/−0.24 | 111+/−20 | 0.5 | 1 | | |
| Mulberry | 1.43+/−0.12 | 107+/−9.0 | 0.51 | | 1 | |
| Mulb + ret. palmitate | 4.84+/−0.61 | 364+/−46 | 0.00074 | 0.0058 | 0.00072 | Yes |
| Mulb + ret. Linoleate | 3.90+/−0.22 | 293+/−16 | 0.00013 | 0.00047 | 0.000007 | Yes |
| Mulb + ret. acetate | 6.5+/−2.07 | 488+/−155 | 0.0126 | 0.014 | 0.0133 | Yes |

TABLE 8

500 nM retinyl esters and 0.001 μl mulberry extract (retinoid: mulberry ratio = 6:1)

| Groups | CRABP-2 levels | As % of control | p value vs. control | p value vs. retinoid | p value vs. mulberry | Synergy |
|---|---|---|---|---|---|---|
| Control | 1.33+/−0.21 | 100+/−15 | 1 | | | |
| Retinyl Palmitate | 1.43+/−0.2 | 107+/−15 | 0.57 | 1 | | |
| Retinyl linoleate | 2.13+/−0.02 | 160+/−2 | 0.01 | 1 | | |
| Retinyl acetate | 2.045+/−0.06 | 153+/−5.0 | 0.02 | 1 | | |
| Mulberry | 1.43+/−0.12 | 107+/−9.0 | 0.51 | | 1 | |
| Mulb + ret. palmitate | 3.25+/−0.67 | 244+/−50 | 0.009 | 0.01 | 0.00019 | Yes |

TABLE 8-continued 500 nM retinyl esters and 0.001 μl mulberry extract (retinoid: mulberry ratio = 6:1)

| Groups | CRABP-2 levels | As % of control | p value vs. control | p value vs. retinoid | p value vs. mulberry | Synergy |
|---|---|---|---|---|---|---|
| Mulb + ret. Linoleate | 3.39+/−0.41 | 255+/−31 | 0.00015 | 0.0026 | 0.000014 | Yes |
| Mulb + ret. acetate | 3.75+/−0.28 | 282+/−21 | 0.00027 | 0.0039 | 0.00019 | Yes |

TABLE 9

10 μM retinyl esters and 0.01 μl mulberry extract (retinoid: mulberry ratio = 12:1)

| Groups | CRABP-2 levels | As % of control | p value vs. control | p value vs. retinoid | p value vs. mulberry | Synergy |
|---|---|---|---|---|---|---|
| Control | 1.27+/−0.06 | 100+/−5.0 | 1 | | | |
| Retinyl Palmitate | 2.75+/−0.33 | 216+/−26 | 0.0016 | 1 | | |
| Retinyl linoleate | 1.8+/−0.29 | 142+/−23 | 0.037 | 1 | | |
| Retinyl acetate | 2.65+/−0.49 | 208+/−39 | 0.0089 | 1 | | |
| Mulberry | 1.48+/−0.35 | 117+/−27 | 0.351 | | 1 | |
| Mulb + ret. palmitate | 4.06+/−1.3 | 319+/−109 | 0.032 | 0.189 | 0.045 | No |
| Mulb + ret. Linoleate | 5.59+/−0.59 | 440+/−46 | 0.00085 | 0.0022 | 0.002 | Yes |
| Mulb + ret. acetate | 5.5+/−1.4 | 433+/−111 | 0.011 | 0.04 | 0.014 | Yes |

TABLE 10

10 μM retinyl esters and 0.001 μl mulberry extract (retinoid: mulberry ratio = 120:1)

| Groups | CRABP-2 levels | As % of control | p value vs. control | p value vs. retinoid | p value vs. mulberry | Synergy |
|---|---|---|---|---|---|---|
| Control | 1.27+/−0.06 | 100+/−5.0 | 1 | | | |
| Retinyl Palmitate | 2.75+/−0.33 | 216+/−26 | 0.0016 | 1 | | |
| Retinyl linoleate | 1.80+/−0.29 | 142+/−23 | 0.037 | 1 | | |
| Retinyl acetate | 2.65+/−0.49 | 208+/−39 | 0.0089 | 1 | | |
| Mulberry | 1.48+/−0.35 | 117+/−27 | 0.351 | | 1 | |
| Mulb + ret. palmitate | 3.37+/−0.43 | 265+/−33 | 0.0011 | 0.121 | 0.0087 | No |
| Mulb + ret. Linoleate | 3.85+/−1.17 | 303+/−92 | 0.018 | 0.042 | 0.026 | Yes |
| Mulb + ret. acetate | 6.74+/−1.8 | 530+/−120 | 0.034 | 0.043 | 0.014 | Yes |

TABLE 11

| Retinoid: Mulberry Ratio | Retinyl-Linoleate | Retinyl-Palmitate | Retinyl-Acetate |
|---|---|---|---|
| 1:80 | No | no | Yes (1 μM: 1 μl) |
| 1:16 | no | Yes (500 nM: 0.1 μl) | Yes (500 nM: 0.1 μl) |
| 1:8 | Yes (1 μM: 0.1 μl) | Yes (1 μM: 0.1 μl) | Yes (1 μM: 0.1 μl) |
| 1:1.6 | Yes (500 nM: 0.01 μl) | Yes (500 nM: 0.01 μl) | Yes (500 nM: 0.01 μl) |
| 1.2:1 | Yes (100 nM: 0.001 μl) | Yes (100 nM: 0.001 μl) | Yes (100 nM: 0.001 μl) |
| 6:1 | Yes (500 nM: 0.001 μl) | Yes (500 nM: 0.001 μl) | Yes (500 nM: 0.001 μl) |
| 12:1 | Yes (10 μM: 0.01 μl) | No | Yes (10 μM: 0.01 μl) |
| 120:1 | Yes (10 μM: 0.001 μl) | no | Yes (10 μM: 0.001 μl) |

In summary, retinyl acetate showed synergy with mulberry extract at a ratio between 1:80 and 120:1 in skin cells. Retinyl linoleate showed synergy between 1:8 and 120:1 and retinyl palmitate showed synergy between ratios 1:16 and 6:1.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin care composition comprising:
   (i) a glycolic extract of mulberry root in an amount of from 0.00001 to 10 wt. %,
   (ii) a retinoid selected from the group consisting of retinyl acetate, retinyl palmitate and retinyl linoleate, and
   (iii) a cosmetically acceptable vehicle, wherein the weight ratio of retinyl acetate to the mulberry extract is in the range of from 1:80 to 120:1, the weight ratio of retinyl linoleate to the mulberry extract is in the range of from 1:8 to 120:1, and the weight ratio of retinyl palmitate to the mulberry extract is in the range of from 1:16 to 6:1.

2. A cosmetic method of improving the appearance of wrinkled, lined, dry, flaky, aged or photodamaged skin and improving skin thickness, elasticity, flexibility and plumpness, the method comprising applying to the skin the composition of claim 1.

3. A cosmetic method of increasing the level of cellular retinoic acid binding protein in the skin fibroblasts, the method comprising applying to the skin the composition of claim 1.

* * * * *